United States Patent [19]

Golub et al.

[11] 4,366,144

[45] Dec. 28, 1982

[54] IN VIVO METHOD OF DETERMINING LEUCOCYTE MIGRATORY ACTIVITY LEVELS

[75] Inventors: Lorne M. Golub, Smithtown; Ralph S. Kaslick, New York, both of N.Y.

[73] Assignee: Research Foundation of State Univ. of NY, Albany, N.Y.

[21] Appl. No.: 117,353

[22] Filed: Jan. 31, 1980

[51] Int. Cl.$^3$ .................... A61K 49/00; G01N 33/48; G01N 33/50
[52] U.S. Cl. ......................................... 424/9; 424/49; 424/177; 436/530; 436/811
[58] Field of Search .................... 424/8, 9, 12, 49, 177

[56] References Cited

PUBLICATIONS

Golub et al., Chem. Abs., vol. 85, 1976, Ab. No. 85:175020p.
Ramamurthy, Siegel, Iacono & Golub, J. Periodont Res., vol. 14, Jul. 1979, pp. 289–296.
Hase, J. Periodontal Res., vol. 14, 1979, pp. 153–159.
Budtz-Jörgensen, J. Periodontal Res., vol. 12, 1977, pp. 21–29.
Kraal, J. Periodontal Res., vol. 12, 1977, pp. 242–249.
Golub, Oral Sci. Rev., vol. 8, 1976, pp. 49–61.

*Primary Examiner*—Anna P. Fagelson
*Attorney, Agent, or Firm*—Omri M. Behr

[57] ABSTRACT

Pharmacologically acceptable chemotactic agents when applied to gingival crevices cause the migration of crevicular fluid containing crevicular leucocytes into the said gingival crevice.

A quantitative correlation has been found between the amount of crevicular fluid migrating into the crevice and the crevicular fluid migrating into the crevice and the crevicular leucocytes contained therein after chemotactic challenge.

It has further been shown that the amount of fluid and leucocytes migrating into said crevice gave a predictable relationship to the migratory activity of leucocytes obtained from the same subject when measured by conventional in vitro means.

A rapid, convenient and simple method is thus provided for detecting certain diseases involving leucocyte migratory activity abnormalities for example diabetes mellitus and periodontosis.

7 Claims, 8 Drawing Figures

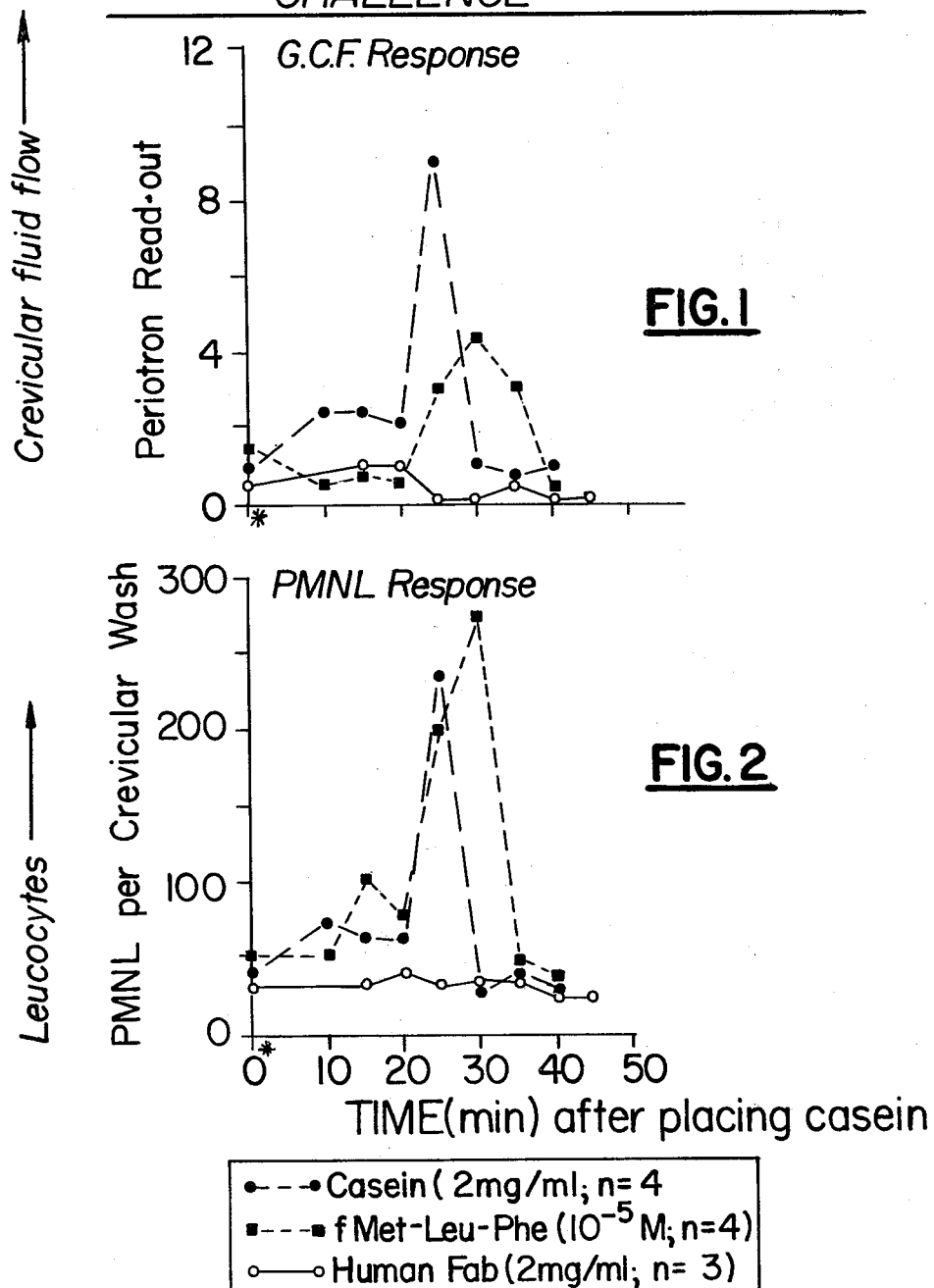

○——○ Casein (2mg/ml)
■---■ Fab (2mg/ml) } control or
○— —○ Buffer     } inactive substances

* Chemotactic Challenge

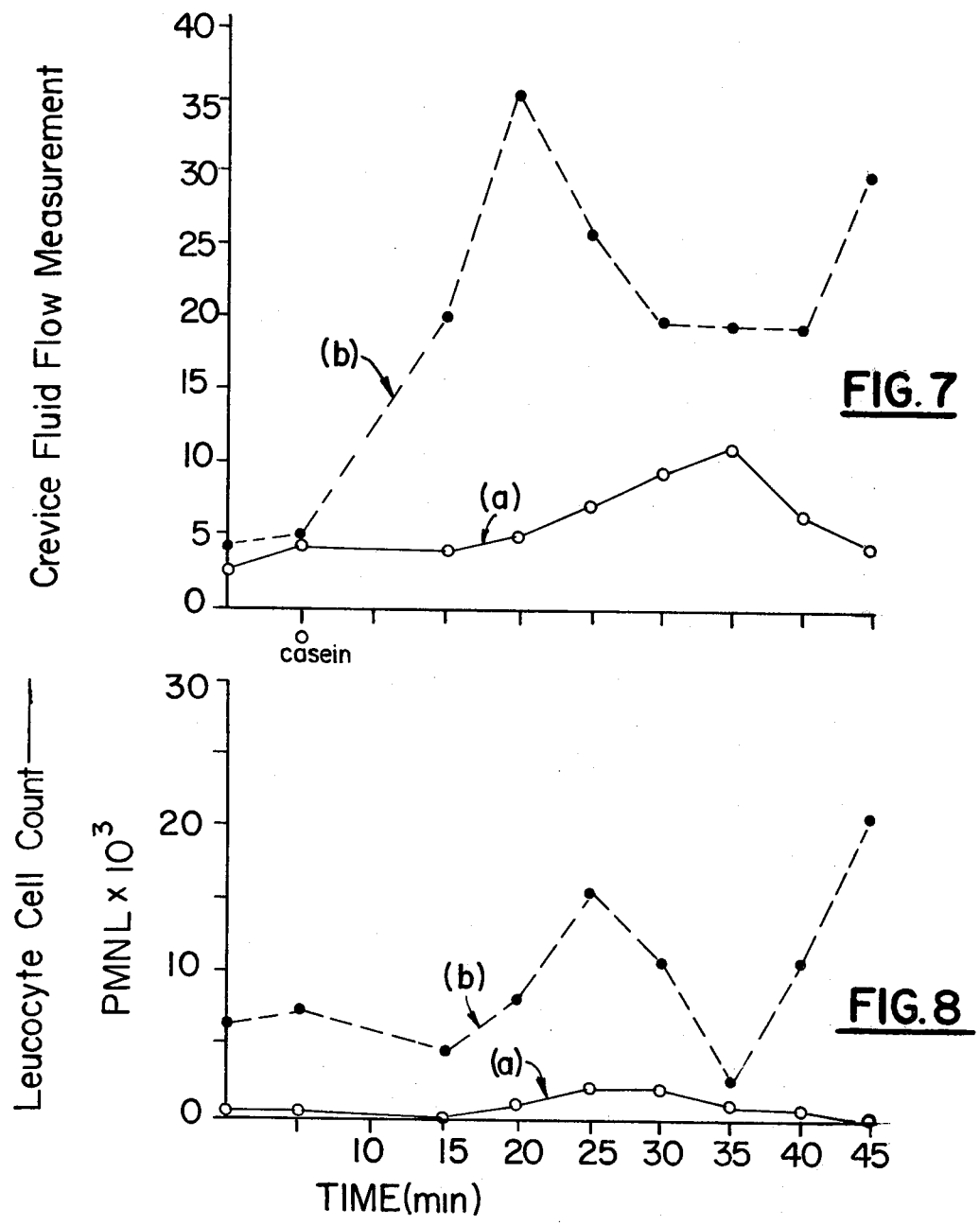
Curve (a) = 5 normal humans (average of 5 at each time point)
Curve (b) = 3 patients with "Periodontosis" [severe localized gum disease associated with leucocyte migratory defect]

IN VIVO METHOD OF DETERMINING LEUCOCYTE MIGRATORY ACTIVITY LEVELS

BACKGROUND OF THE INVENTION

Field of the Invention

Leucocytes are body cells present in blood fluids which are part of the defense mechanism of mammalian systems. By mechanisms which are not entirely understood, leucocytes are attracted to foreign bacteria towards which they migrate and which, by certain means not relevant to the present invention, they ultimately destroy.

The rate at which the leucocytes migrate is related to the viability of the defense mechanism of any given mammalian system. It is known that in certain diseases this migratory activity is either impaired or abnormal. Among the diseases may be mentioned diabetes mellitus and periodontosis.

In vitro methods of measurement of leucocyte migratory activity are well known. One of these methods are set forth in some detail in *J. Periodont Res.* 14, 289-296 (1979). Briefly summarized, these methods involve the finding that certain substances, typically proteins or peptides have the ability to simulate the bacterial attraction and cause directed migration of the leucocytes. Such agents are known as chemotactic agents.

In the in vitro method, a sample of the patient's blood is taken. The sample is then reacted by methods well known in the art to remove first the red blood cells and thereafter to isolate the appropriate leucocytes. A test bed comprising, suitably, a Petrie dish filled with a suitable gel and having wells cut therein is then prepared. The chemotactic agent at a predetermined level of dilution is put into certain of these wells and the leucocytes from the test subject also diluted to a predetermined level are put into wells adjacent to those wells containing the chemotactic agent. The test medium is then incubated and after a predetermined time, the distance moved through the medium towards the chemotactic agent by the leucocytes is measured.

It will be understood that this procedure is extremely time consuming and it would be highly desirable to obtain the information yielded by these experiments in a more rapid manner.

SUMMARY OF THE INVENTION

Applicants herein have made the surprising finding that leucocytes can be caused to rapidly reproducably, and measurably migrate into gingival crevices under the influence of a chemotactic agent applied to said crevices.

In the practice of the present invention, a small predetermined amount of a pharmacologically acceptable chemotactic agent at a predetermined level of dilution is applied to a gingival crevice of a subject, suitably by inserting a wire loop of a predetermined size carrying a solution of the said chemotactic agent. The crevicular fluid in said gingival crevice is then removed at predetermined times and the volume of crevicular fluid as well as its leucocyte content is measured and plotted. At suitable levels of application of the chemotactic agent well defined peaks are noted which can be and have been correlated to leucocyte migratory activity.

It has also been found that the volume of crevicular fluid migrating into the gingival crevice under the influence of the chemotactic agent has a directly determinable relationship to the number of leucocytes which it contains.

It has been found that subjects suffering from diabetes mellitus show a peak approximately 40% lower than the peak found in subjects without this metabolic defect. This difference in peak height correlates closely to the drop in leucocyte migratory activity found by the in vitro test for such activity.

In the case of subjects suffering from periodontosis a most unusual and characteristic double peak was noted.

DESCRIPTION OF THE PREFERRED EMBODIMENT

The method of the present invention involves the determination of leucocyte migration into the gingival crevices of test subjects under the influence of chemotactic agents.

In the method of the present invention, gingival crevices of test subjects were examined to determine base line values for crevicular leucocytes and crevicular fluid. The volume of crevicular fluid was collected on filter paper strips and measured with a fluid meter in accordance with the procedures set forth in U.S. Pat. No. 3,753,099.

The crevices were washed with a suitable isotonic solution, for example HBSS, approximately 10 micro liters of wash being utilized for each reading, and the number of leucocytes measured by methods well known in the art in a hemacytometer (Spaski-Lehner *J. Periodont. Res.* 11, 19, (1976)). The chemotactic agent is then applied to the subject crevices. Any pharmaceutically acceptable chemotactic agent may be employed. Especially preferred is casein since casein is entirely safe at any dosage levels. A particularly effective chemotactic agent which is safe at the quantities and levels of dilution utilized is the synthetic tripeptide F-Met-Phe-Leu.

The chemotactic agent is diluted to a suitable level. In test experiments it has been found, for casein that the increase of leucocyte level in the gingival crevice is negligible at a dilution of 0.01 mg/ml, exceeds base line by a factor of 2 at a level of 0.25 mg/ml and at levels of 0.5 mg/ml through 4 mg/ml gives a response approximately seven times base line. Hence, a suitable level of dilution is between about 0.5 through 4 mg/ml most suitably about 2 mg/ml (in an isotonic medium such as HBSS).

The volume of a gingival crevice varies greatly in accordance with the health condition of the gingiva of the test subject. The volume of the crevice will usually not exceed 1 microliter and, in any event, at the dosage levels utilized, the surface tension effects will be sufficient to localize both the applied solutions of chemotactic agent and the crevical fluid passing into the crevice. It has been found that the application of between 0.2 and 0.8 most suitably 0.6 microliters of the chemotactic agent at the foregoing levels of dilution is most suitable. While the present invention is not limited thereto, it has been found that this volume of fluid is most readily applied by preparing a wire loop which is then inserted into a solution of the chemotactic agent. The surface tension effects in the loop will pick up at a substantially constant and reproducible amount of the chemotactic agent. Since the amount of chemotactic agent applied to the crevice is not, within the limits of experimentation, critical, the level of reproducability obtained by this method is entirely sufficient.

After application of the chemotactic agent to the gingival crevice of the test subject, crevicular fluid volume and crevicular leucocyte amounts are monitored after a predetermined time. It has been found suitable to make the first measurement approximately fifteen minutes after the application of the chemotactic agent and repeat measurements at approximately five minute intervals thereafter up to approximately forty-five minutes.

It has been found that peak values of both factors occur at between about twenty-five to about thirty-five minutes after application of the chemotactic agent.

In certain such experiments on healthy human subjects it has been found that the crevicular fluid volume increased 104% over base line in 34± 1 minute and the crevicular leucocyte levels increased 881% in 29± 2 minutes.

Casein and the specific tripeptide F-Met-Phe-Leu in gingival crevices produced analogous responses. In both humans and rats application of HBSS without casein produced no rise in either the crevicular leucocyte level or the volume of crevicular fluid.

It is well known that the rat is a good test model for diabetes mellitus in humans. In test rats it is possible to induce diabetes mellitus in order to study the effects of pharmaceutically active agents on the condition.

It has been shown (J. Periodont. Res. 14, 289-296 (1979)) that utilizing the in vitro test for leucocyte migratory activity, leucocytes obtained from rats having artificially induced diabetes mellitus showed a loss of approximately 40% in migratory activity. This is substantially the same level of loss of migratory activity in leucocytes obtained from human subject suffering from the same metabolic malfunction.

In the test experiments carried out in accordance with the present invention, the level of crevicular leucocyte amounts and crevicular fluid in rats having artificially induced diabetes mellitus showed a drop in peak amounts as discussed above of approximately 40% of the peak values for undiseased rats.

BRIEF DESCRIPTION OF THE DRAWINGS

FIG. 1 is a graph showing a plot of crevicular fluid flow against time in a healthy rat challenge.

FIG. 2 is a graph showing a plot of crevicular leucocyte count in a healthy rat challenge.

FIG. 7 is a graph showing a plot of crevicular fluid flow against time in human periodontosis patients.

FIG. 8 is a graph showing a plot of crevicular leucocyte count in human periodontosis patients.

GENERAL PROCEDURES

The following general procedures were utilized both in the rat experiments and the human experiments.

Two adjacent gingival crevices were washed with water, isolated from contact with other sections of the mouth and air dried. The crevices were then subjected to a sulcular wash in accordance with the technique of Spaski-Lehner, (J. Periodont. Res. 11 19 (1976)). The leucocytes in the wash were counted with a hemocytometer and recorded. Sulcular fluid was then collected from both adjacent crevices on a sterile filter paper strip and the strips and volume measured on an electronic GCF meter (Harco Electronics, Winnipeg, Canada, U.S. Pat. No. 3,753,099; Golub and Kleinberg, Oral Sciences Reviews 8 49 through 61 (1976)). In order to obtain base line values, fluid was again collected. From one sulcus the volume of fluid was collected and measured and from the other the number of leucocytes collected was measured. The chemotactic agent utilized was then placed into both sulci with a wire loop carrying a predetermined volume of chemotactic agent at a predetermined dilution. The contact time is designated time zero. Extreme care is taken to keep the field isolated. After fifteen minutes the first readings are taken with subsequent readings at five minute intervals. Fluid is collected and volume thereof measured from one sulcus and the fluid from the other sulcus utilized for leucocyte count.

EXAMPLE 1

HEALTHY RAT RESPONSE

Four rats (Sprague Dawley) were used in the casein challenge (0.6 ul 2 mg casein/ml HBSS) similarly four rats were challenged with 0.6 ul of F-Met-Phe-Leu ($10^{-5}$M) and three rats were challenged with human FAB protein. The average results are shown in FIGS. 1 and 2.

FIG. 1 shows the Periotron ® (registered trademark, GCF meter manufactured by Harro Electronics, Winnipeg, Canada) readout indicating crevicular fluid volume plotted against time after challenge. FIG. 2 shows the number of leucocytes per crevicular wash also plotted against time after challenge. It will be seen that both casein and F-Met-Phe-Leu show a substantial response in both curves while human FAB protein used as a control substance shows no peaking.

EXAMPLE 2

HEALTHY HUMAN RESPONSE

Figure 3:
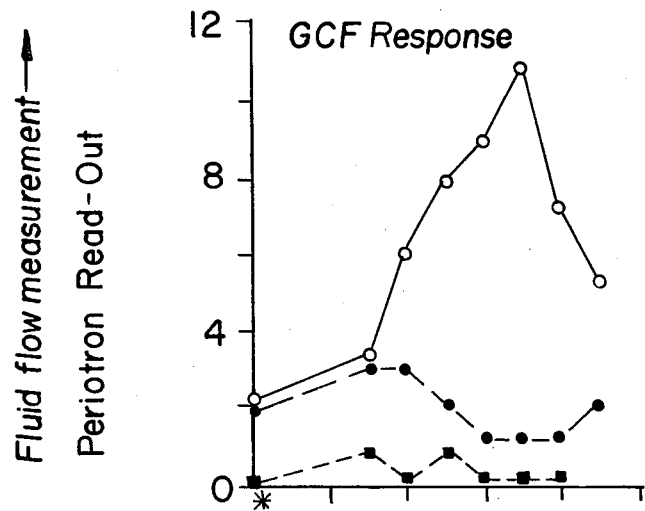
FIG. 3 is a graph showing a plot of crevicular fluid flow against time in a healthy human challenge.
Figure 4:
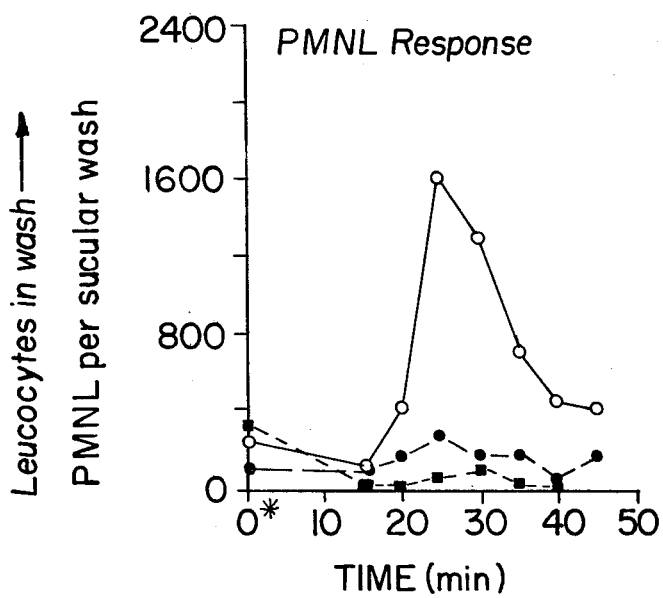
FIG. 4 is a graph showing a plot of crevicular leucocyte count in a healthy human challenge.

The experiments of Example 1 were repeated on five human subjects. In place of a F-Met-Phe-Leu challenge, however, the response to the HBSS buffer itself was measured and found to show no peaking. The results are plotted on FIGS. 3 and 4.

EXAMPLE 3

DIABETIC RAT EXPERIMENT

Figure 6:
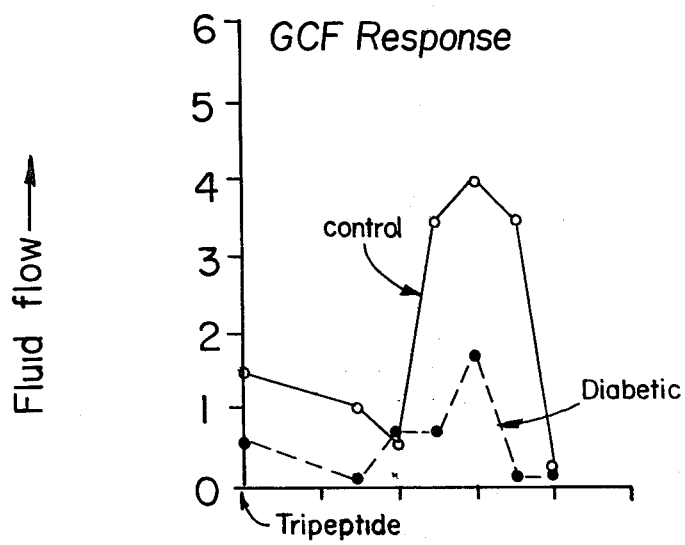
FIG. 6 is a graph showing a plot of crevicular fluid flow against time in a diabetic rat challenge.
Figure 5:
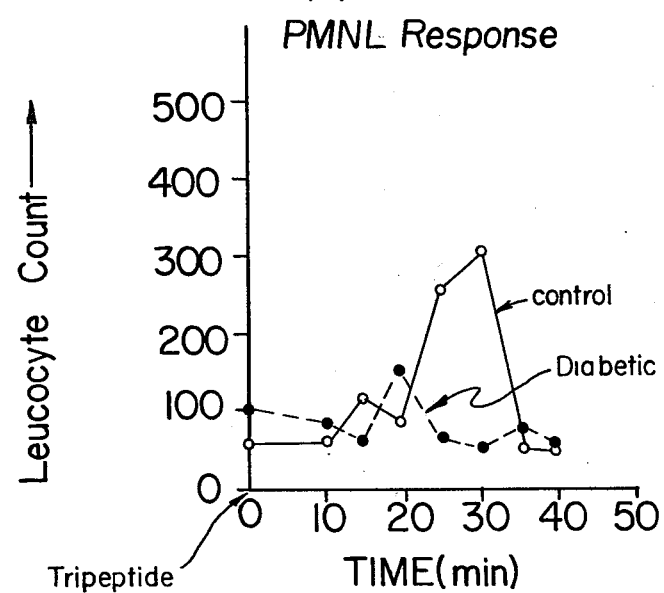
FIG. 5 is a graph showing a plot of crevicular leucocyte count diabetic rat challenge.

Four rats in which diabetes mellitus had been induced by the method of Golub et al, Biochem Biophys Acta 534 73-81 1978 were utilized as test subjects. The rats were challenged with F-Met-Phe-Leu (0.6 ul $10^{-5}$M) and the results plotted on FIG. 6 for flow volume and FIG. 5 for leucocyte count. Peritoneal exudates from these rats were tested by the standard in vitro method and the results set forth in Table 1 below.

FIGURE 1

IN VITRO CHEMOTACTIC ACTIVITY OF NORMAL AND DIABETIC RAT PMNL

|  | Migration Towards Chemotactic Agent (A) | Spontaneous Migration (B) | Chemotactic Index* (A/B) | Chemotactic Differential* (A-B) |
|---|---|---|---|---|
| Normal | 8.5 ± 0.6 | 1.2 ± 0.2 | 7.4 ± 0.6 | 7.3 ± 0.5 |
| Diabetic | 5.5 ± 0.4 | 1.2 ± 0.1 | 4.9 ± 0.4 |  |
| % Reduc- |  |  |  |  |

FIGURE 1-continued

IN VITRO CHEMOTACTIC ACTIVITY OF NORMAL AND DIABETIC RAT PMNL

| Migration Towards Chemotactic Agent (A) | Spontaneous Migration (B) | Chemotactic Index* (A/B) | Chemotactic Differential* (A-B) |
|---|---|---|---|
| tion Due to Diabetes 35 | 0 | 35 | 40 |

*See Nelson et al (1976) In Vitro Methods in Cell Mediated and Tumor Immunity, Academic Press NY, 1976, pages 663-675

As will be seen, all three tests show a drop of leucocyte migratory activity of about 40% between the control and the diabetic rat.

EXAMPLE 4

HUMAN PERIODONTOSIS

Five normal human subjects were used as controls and three human patients suffering from a localized gum disease associated with leucocyte migratory defects known as periodontosis were tested utilizing casein 0.6 ul 2, mg/ml HBSS. The curves obtained are shown in FIGS. 7 and 8 for fluid volume and leucocyte cell count respectively. The patients suffering from periodontosis show an abnormally high double peak in both tests.

Having thus set forth the nature of the invention, what is claimed is:

1. An in vivo method of determining leucocyte migratory activity levels in mammalian subjects comprising the steps of:
   a. Collecting the crevicular fluid from a predetermined gingival crevice after at least one predetermined time interval;
   b. determining the volume of crevicular fluid in a predetermined gingival crevice generated in a predetermined time interval to provide a base level per unit time;
   c. introducing a predetermined amount of a pharmaceutically acceptable chemotactic agent into a gingival crevice of the subject;
   d. collecting the crevicular fluid from said gingival crevice after at least one predetermined time interval following the introduction of said chemotatic agent into the said gingival crevice;
   e. measuring the volume of crevicular fluid collected and
   f. determining the increase in volume of said crevicular fluid collected per unit time over the base level to provide a measure of the leucocyte migratory activity level.

2. A method in accordance with claim 1 wherein the chemotactic agent is the synthetic tripeptide F-Met-Phe-Leu.

3. A method in accordance with claim 1 wherein the chemotactic agent is casein.

4. A method in accordance with claim 3 wherein there is introduced between 0.2 and 0.8 microliters of chemotactic agent at a concentration of at least 0.5 mg/ml of a pharmaceutically acceptable isotonic solution.

5. A method in accordance with claim 1 which comprises carrying out the steps of claim 1 upon a control subject and a test subject and comparing the maximum crevicular fluid volume levels obtained in each case.

6. An in vivo method of determining leucocyte migratory activity levels in mammalian subjects comprising the steps of:
   a. collecting the crevicular fluid from a predetermined gingival crevice after at least one predetermined time interval;
   b. determining the number of crevicular leucocytes generated in a predetermined gingival crevice in a predetermined time interval to provide a base level per unit time;
   c. introducing a predetermined amount of a pharmaceutically acceptable chemotatic agent into a gingival crevice of the subject;
   d. collecting the crevicular fluid from said gingival crevice after at least one predetermined time interval following the introduction of said chemotatic agent into the said gingival crevice;
   e. determining the number of crevicular leucocytes collected and
   f. determining the increase in leucocytes generated in said crevicular fluid collected per unit time over the base level to provide a measure of the leucocyte migratory activity level.

7. A method in accordance with claim 6 which comprises carrying out the steps of claim 10 upon a control subject and a test subject and comparing the maximum number of crevicular leucocytes collected.

* * * * *

UNITED STATES PATENT AND TRADEMARK OFFICE
CERTIFICATE OF CORRECTION

PATENT NO. : 4,366,144
DATED : December 28, 1982
INVENTOR(S) : Lorne M. Golub et al.

It is certified that error appears in the above-identified patent and that said Letters Patent are hereby corrected as shown below:

[75] Inventors: add: Vincent J. Iacono, Medford, NY;
Nungavaram S. Ramamurthy, Smithtown, NY Col. 1, line 41: insert: This invention was made in part with Government support under DE 03987 (May 1975) awarded by National Institute of Dental Research (NIH). The Government has certain rights in this invention.

Signed and Sealed this

Twenty-fifth Day of October 1983

[SEAL]

Attest:

GERALD J. MOSSINGHOFF

Attesting Officer    Commissioner of Patents and Trademarks